United States Patent [19]

Makino et al.

[11] Patent Number: 6,153,648
[45] Date of Patent: Nov. 28, 2000

[54] IODOPROPARGYLAMINE COMPOUNDS, AND INDUSTRIAL ANTIMICROBIAL AND ANTIFUNGAL AGENTS, ALGICIDES, AND ANTIFOULING AGENTS CONTAINING THE SAME

[75] Inventors: Kenji Makino, Tokyo; Shinichi Igarashi; Mitsugu Futagawa, both of Saitama-ken, all of Japan

[73] Assignee: Nissan Chemical Industries, Ltd., Tokyo, Japan

[21] Appl. No.: 09/486,121

[22] PCT Filed: Aug. 27, 1998

[86] PCT No.: PCT/JP98/03806

§ 371 Date: Feb. 23, 2000

§ 102(e) Date: Feb. 23, 2000

[87] PCT Pub. No.: WO99/11601

PCT Pub. Date: Mar. 11, 1999

[30] Foreign Application Priority Data

Aug. 28, 1997 [JP] Japan ................................. 9-232361

[51] Int. Cl.$^7$ .......................... A01N 37/06; A01N 33/04; A01N 41/10; C07C 69/73
[52] U.S. Cl. .......................... 514/547; 514/529; 514/549; 514/671; 514/676; 514/710; 560/128; 560/169; 560/171; 570/189; 568/30; 568/306
[58] Field of Search ...................... 514/529, 547, 514/549, 671, 676, 710; 560/128, 169, 171; 570/189; 568/30, 306

[56] References Cited

U.S. PATENT DOCUMENTS 4,831,179  5/1989  Pomidor .

FOREIGN PATENT DOCUMENTS

B1-42-26603  12/1967  Japan .

*Primary Examiner*—Johann Richter
*Assistant Examiner*—Brian J. Davis
*Attorney, Agent, or Firm*—Oliff & Berridge, PLC

[57] ABSTRACT

Iodopropargylamine compound of the general formula (1):

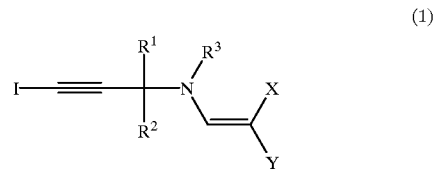

wherein $R^1$ and $R^2$ each independently represent a hydrogen atom or an alkyl group having 1 to 3 carbon atoms, or $R^1$ and $R^2$ combine with each other to form a tetramethylene group or a pentamethylene group, $R^3$ represents a hydrogen atom or an alkyl group having 1 to 3 carbon atoms, and X and Y each independently represent a cyano group, an alkoxycarbonyl group having 2 to 7 carbon atoms, an alkylcarbonyl group having 2 to 7 carbon atoms, an alkylsulfonyl group having 1 to 6 carbon atoms, a phenylcarbonyl group or a phenylsulfonyl group, provided that the phenyl group of a phenylcarbonyl group or a phenylsulfonyl group may be optionally substituted by halogen atoms, alkyl groups having 1 to 3 carbon atoms, alkoxy groups having 1 to 3 carbon atoms, nitro groups or trifluoromethyl groups. The compound are useful as the active ingredient for industrial antibacterial and antifungal agents, algicides, and agents for preventing adhesion of organisms.

8 Claims, No Drawings

6,153,648

IODOPROPARGYLAMINE COMPOUNDS, AND INDUSTRIAL ANTIMICROBIAL AND ANTIFUNGAL AGENTS, ALGICIDES, AND ANTIFOULING AGENTS CONTAINING THE SAME

This application is a 371 of PCT/JP98/03806 filed Aug. 27, 1998.

TECHNICAL FIELD

The present invention relates to an antibacterial and antifungal agent and algicide for industrial products, to an antibacterial and antifungal agent and algicide for using in the production process of industrial products, and to agent for preventing adhesion of organisms for preventing the adhesion of harmful aquatic organisms such as shellfishes.

BACKGROUND ART

An industrial antibacterial and antifungal agent and algicide are used to eliminate various evil influences caused by the growth and propagation of bacteria, fungi and algae at various kinds of industrial products and industrial facilities.

Heretofore, organic nitrogen compounds, organic nitrogen sulfur compounds, organic halogen compounds, nitrogen-containing aliphatic polymers and heavy metal coordination compounds have been used as the industrial antibacterial and antifungal agent and algicide.

An agent for preventing adhesion of organisms is used to prevent harmful aquatic organisms such as shellfish from adhering to fishing nets, bottoms of ships, equipment placed in the sea such as buoys, marine constructions, condensers of cooling water systems at thermal or nuclear power plants, inlet channels of cooling water for heat exchangers of the chemical industry, underwater constructions, reservoirs or the like.

When aquatic organisms are adhered to culturing nets, openings of the nets are clogged, resulting in a decrease of circulation of seawater to inhibit growth of cultured fish, and in many occurrences of fish diseases.

The adhesion of aquatic organisms to ships causes an increase in fluid resistance with the result of a reduction in sailing speed, increase in fuel consumption and costs for cleaning the bottom of the ship and a loss caused by the suspension of service.

The adhesion of aquatic organisms to marine equipment, or marine or water constructions invites an increase in weight and remarkable in convenience in handling operation. The adhesion of aquatic organisms to inlet channels causes a decrease in thermal conductivity, and also causes the problems that the inlet channels are clogged, and the amount of intake water is decreased.

Heretofore, to prevent the adhesion and propagation of seawater organisms and freshwater organisms, an antifouling coating containing an organotin compound such as bis(tributyltin) oxide, or a copper compound such as copper sulfate or cuprous oxide has been used.

The iodopropargyl amine compound of the present invention is a novel compound and it is quite unknown that such compound is effective as an industrial antibacterial and antifungal agent, algicide and agent for preventing adhesion of organisms.

(Problems to be solved by the Invention)

The above-described organic nitrogen compounds, organic nitrogen sulfur compounds, organic halogen compounds, nitrogen-containing aliphatic polymers and heavy metal coordination compounds include those chemicals which are stimulative and cause a problem from a view point of the Labor Safety Law, those chemicals which are used in large doses and cause a problem from a view point of environmental protection, those chemicals which release formalin or halogens and have the possibility of environmental pollution and an influence upon the human body and those chemicals which have the possibility of environmental pollution with a heavy metal. Therefore, it cannot be said that all the industrial antibacterial and antifungal agents and algicides are composed of favorable chemicals only.

Although the above organotin compound as an agent for preventing adhesion of organisms is effective in preventing the adhesion of aquatic organisms, it has high toxicity, accumulates in particular in the body of fishes or shellfishes remarkably and is now regulated because it promotes environmental pollution.

For example, in the United States of America, use of organotin-based ship paints is prohibited to ships as long as 65 feet or less by the Organic Tin Antifouling Paint Regulation (1987), and in the United Kingdom, use of tributyltin-containing agents for preventing adhesion of organisms to ships as long as 25 m or less and marine agriculture is prohibited by the Food and Environmental Protection Law (1987).

In Japan, tributyltin oxide is designated as a specified chemical substance of the first kind, and triphenyltin compounds and tributyltin compounds are designated as specified chemical substances of the second kind by the Chemical Substance Examination Rule (1990). Thus, use of these compounds in fishing nets is prohibited.

Further, it is also taken a measure for the control of use of tributyltin-based paints in the bottom of a ship (Notification by the Ministry of Transport, 1990).

The above copper compounds are widely used in antifouling coatings for inlet channels and bottoms of ships. However, since the copper compounds contain, like tin compounds, copper which is a heavy metal, the use thereof is anxious for environmental pollution in future. Therefore, it cannot be said that the copper compounds are favorable agents for preventing adhesion of organisms.

The compound used in the present invention is not specified in the above regulation law and it is unknown that an iodopropargylamine compound is effective as an industrial antibacterial and antifungal agent, algicide and agent for preventing adhesion of organisms.

SUMMARY OF THE INVENTION

The inventors of the present invention have conducted intensive studies to solve the above problems and have found that a novel iodopropargylamine compound can be an industrial antibacterial and antifungal agent, algicide and agent for preventing adhesion of organisms which has high safety, exhibits a wide spectrum with a small amount from a view point of prevention of environmental pollution and has high practical applicability. Thus, the present invention has been accomplished based on these findings.

That is, the present invention relates to an iodopropargylamine compound of the general formula (1):

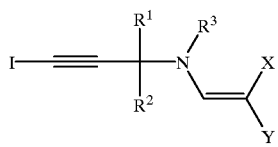

(1)

wherein R¹ and R² each independently represent a hydrogen atom or an alkyl group having 1 to 3 carbon atoms, or R¹ and R² combine with each other to form a tetramethylene group or a pentamethylene group, R³ represents a hydrogen atom or an alkyl group having 1 to 3 carbon atoms, and X and Y each independently represent a cyano group, an alkoxycarbonyl group having 2 to 7 carbon atoms, an alkylcarbonyl group having 2 to 7 carbon atoms, an alkylsulfonyl group having 1 to 6 carbon atoms, a phenylcarbonyl group or a phenylsulfonyl group, provided that the phenyl group of a phenylcarbonyl group or a phenylsulfonyl group may be optionally substituted by halogen atoms, alkyl groups having 1 to 3 carbon atoms, alkoxy groups having 1 to 3 carbon atoms, nitro groups or trifluoromethyl groups, and to an industrial antibacterial and antifungal agent, algicide and agent for preventing adhesion of organisms characterized by containing the same as an active ingredient.

Each of the substituents shown in the general formula (1) will be described in concrete terms.

In the specification, "n" means normal, "i" iso, "s" secondary and "t" tertiary.

Examples of the halogen atom are fluorine, chlorine, bromine and iodine.

Examples of the alkyl group having 1 to 3 carbon atoms are methyl, ethyl, n-propyl, i-propyl and cyclopropyl.

Examples of the alkoxy group having 1 to 3 carbon atoms are methoxy, ethoxy, n-propoxy, i-propoxy and cyclopropoxy.

Examples of the alkoxycarbonyl group having 2 to 7 carbon atoms include methoxycarbonyl, ethoxycarbonyl, n-propoxycarbonyl, i-propoxycarbonyl, cyclopropoxycarbonyl, n-butoxycarbonyl, i-butoxycarbonyl, s-butoxycarbonyl, t-butoxycarbonyl, cyclobutoxycarbonyl, 1-methyl-cyclopropoxycarbonyl, 2-methyl-cyclopropoxycarbonyl, n-pentyloxycarbonyl, 1-methyl-n-butoxycarbonyl, 2-methyl-n-butoxycarbonyl, 3-methyl-n-butoxycarbonyl, 1,1-dimethyl-n-propoxycarbonyl, 1,2-dimethyl-n-propoxycarbonyl, 2,2-dimethyl-n-propoxycarbonyl, 1-ethyl-n-propoxycarbonyl, cyclopentyloxycarbonyl, 1-methyl-cyclobutoxycarbonyl, 2-methyl-cyclobutoxycarbonyl, 3-methyl-cyclobutoxycarbonyl, 1,2-dimethyl-cyclopropoxycarbonyl, 2,3-dimethyl-cyclopropoxycarbonyl, 1-ethyl-cyclopropoxycarbonyl, 2-ethyl-cyclopropoxycarbonyl, n-hexyloxycarbonyl, 1-methyl-n-pentyloxycarbonyl, 2-methyl-n-pentyloxycarbonyl, 3-methyl-n-pentyloxycarbonyl, 4-methyl-n-pentyloxycarbonyl, 1,2-dimethyl-n-butoxycarbonyl, 1,2-dimethyl-n-butoxycarbonyl, 1,3-dimethyl-n-butoxycarbonyl, 2,2-dimethyl-n-butoxycarbonyl, 2,3-dimethyl-n-butoxycarbonyl, 3,3-dimethyl-n-butoxycarbonyl, 1-ethyl-n-butoxycarbonyl, 2-ethyl-n-butoxycarbonyl, 1,1,2-trimethyl-n-propoxycarbonyl, 1,2,2-trimethyl-n-propoxycarbonyl, 1-ethyl-1-methyl-n-propoxycarbonyl, 1-ethyl-2-methyl-n-propoxycarbonyl, 2-ethyl-2-methyl-n-propoxycarbonyl, cyclohexyloxycarbonyl, 1-methyl-cyclopentyloxycarbonyl, 2-methyl-cyclopentyloxycarbonyl, 3-methyl-cyclopentyloxycarbonyl, 1-ethyl-cyclobutoxycarbonyl, 2-ethyl-cyclobutoxycarbonyl, 3-ethyl-cyclobutoxycarbonyl, 1,2-dimethyl-cyclobutoxycarbonyl, 1,3-dimethyl-cyclobutoxycarbonyl, 2,2-dimethyl-cyclobutoxycarbonyl, 2,3-dimethyl-cyclobutoxycarbonyl, 2,4-dimethyl-cyclobutoxycarbonyl, 3,3-dimethyl-cyclobutoxycarbonyl, 1-n-propyl-cyclopropoxycarbonyl, 2-n-propyl-cyclopropoxycarbonyl, 1-i-propyl-cyclopropoxycarbonyl, 2-i-propyl-cyclopropoxycarbonyl, 1,2,2-trimethyl-cyclopropoxycarbonyl, 1,2,3-trimethyl-cyclopropoxycarbonyl, 2,2,3-trimethyl-cyclopropoxycarbonyl, 1-ethyl-2-methyl-cyclopropoxycarbonyl, 2-ethyl-1-methyl-cyclopropoxycarbonyl, 2-ethyl-2-methyl-cyclopropoxycarbonyl, 2-ethyl-3-methyl-cyclopropoxycarbonyl and the like.

Examples of the alkylcarbonyl group having 2 to 7 carbon atoms include methylcarbonyl, ethylcarbonyl, n-propylcarebonyl, i-propylcarbonyl, cyclopropylcarbonyl, n-butylcarbonyl, i-butylcarbonyl, s-butylcarbonyl, t-butylcarbonyl, cyclobutylcarbonyl, 1-methyl-cyclopropylcarbonyl, 2-methyl-cyclobutylcarbonyl, n-pentylcarbonyl, 1-methyl-n-butylcarbonyl, 2-methyl-n-butylcarbonyl, 3-methyl-n-butylcarbonyl, 1,1-dimethyl-n-propylcarbonyl, 1,2-dimethyl-n-propylcarbonyl, 2,2-dimethyl-n-propylcarbonyl, 1-ethyl-n-propylcarbonyl, cyclopentylcarbonyl, 1-methyl-cyclobutylcarbonyl, 2-methyl-cyclobutylcarbonyl, 3-methyl-cyclobutylcarbonyl, 1,2-dimethyl-cyclopropylcarbonyl, 2,3-dimethyl-cyclopropylcarbonyl, 1-ethyl-cyclopropylcarbonyl, 2-ethyl-cyclopropylcarbonyl, n-hexylcarbonyl, 1-methyl-n-pentylcarbonyl, 2-methyl-n-pentylcarbonyl, 3-methyl-n-pentylcarbonyl, 4-methyl-n-pentylcarbonyl, 1,1-dimethyl-n-butylcarbonyl, 1,2-dimethyl-n-butylcarbonyl, 1,3-dimethyl-n-butylcarbonyl, 2,2-dimethyl-n-butylcarbonyl, 2,3-dimethyl-n-butylcarbonyl, 3,3-dimethyl-n-butylcarbonyl 1-ethyl-n-butylcarbonyl, 2-ethyl-n-butylcarbonyl, 1,1,2-trimethyl-n-propylcarbonyl, 1,2,2-trimethyl-n-propylcarbonyl, 1-ethyl-1-methyl-n-propylcarbonyl, 1-ethyl-2-methyl-n-propylcarbonyl, 2-ethyl-2-methyl-n-propylcarbonyl, cyclohexylcarbonyl, 1-methyl-cyclopentylcarbonyl, 2-methyl-cyclopentylcarbonyl, 3-methyl-cyclopentylcarbonyl, 1-ethyl-cyclobutylcarbonyl, 2-ethyl-cyclobutylcarbonyl, 3-ethyl-cyclobutylcarabonyl, 1,2-dimethyl-cyclobutylcarbonyl, 1,3-dimethyl-cyclobutylcarbonyl, 2,2-dimethyl-cyclobutylcarbonyl, 2,3-dimethyl-cyclobutylcarbonyl, 2,4-dimethyl-cyclobutylcarbonyl, 3,3-dimethyl-cyclobutylcarbonyl, 1-n-propyl-cyclopropylcarbonyl, 2-n-propyl-cyclopropylcarbonyl, 1-i-propyl-cyclopropylcarbonyl, 2-i-propyl-cyclopropylcarbonyl, 1,2,2-trimethyl-cyclopropylcarbonyl, 1,2,3-trimethyl-cyclopropylcarbonyl, 2,2,3-trimethyl-cyclopropylcarbonyl, 1-ethyl-2-methyl-cyclopropylcarbonyl, 2-ethyl-1-methyl-cyclopropylcarbonyl, 2-ethyl-2-methyl-cyclopropylcarbonyl, 2-ethyl-3-methyl-cyclopropylcarbonyl and the like.

Examples of the alkylsulfonyl group having 1 to 6 carbon atoms include methylsulfonyl, ethylsulfonyl, n-propylsulfonyl, i-propylsulfonyl, cyclopropylsulfonyl, n-butylsulfonyl, i-butylsulfonyl, s-butylsulfonyl, t-butylsulfonyl, cyclobutylsulfonyl, 1-methyl-cyclopropylsulfonyl, 2-methyl-cyclopropylsulfonyl, n-pentylsulfonyl, 1-methyl-n-butylsulfonyl, 2-methyl-n- butylsulfonyl, 3-methyl-n-butylsulfonyl, 1,1-dimethyl-n-propylsulfonyl, 1,2-dimethyl-n-propylsulfonyl, 2,2-dimethyl-n-propylsulfonyl, 1-ethyl-n-propylsulfonyl, cyclopentylsulfonyl, 1-methyl-cyclobutylsulfonyl, 2-methyl-cyclobutylsulfonyl, 3-methyl-cyclobutylsulfonyl, 1,2-dimethyl-cyclopropylsulfonyl, 2,3-dimethyl-cyclopropylsulfonyl, 1-ethyl-cyclopropylsulfonyl, 2-ethyl-cyclopropylsulfonyl, n-hexylsulfonyl, 1-methyl-n-pentylsulfonyl, 2-methyl-n-pentylsulfonyl, 3-methyl-n-pentylsulfonyl, 4-methyl-n-pentylsulfonyl, 1,1-dimethyl-n-butylsulfonyl, 1,2-dimethyl-n-butylsulfonyl, 1,3-dimethyl-n-butylsulfonyl, 2,2-dimethyl-n-butylsulfonyl, 2,3-dimethyl-n-butylsulfonyl, 3,3-dimethyl-n-butylsulfonyl, 1-ethyl-n-butylsulfonyl, 2-ethyl-n-butylsulfonyl, 1,1,2-trimethyl-n-propylsulfonyl, 1,2,2-trimethyl-n-propylsulfonyl, 1-ethyl-1-methyl-n-propylsulfonyl, 1-ethyl-2-methyl-n-propylsulfonyl, 2-ethyl-2-methyl-n-propylsulfonyl, cyclohexylsulfonyl, 1-methyl-cyclopentylsulfonyl, 2-methyl-cyclopentylsulfonyl, 3-methyl-cyclopentylsulfonyl, 1-ethyl-cyclobutylsulfonyl, 2-ethyl-cyclobutylsulfonyl, 3-ethyl-cyclobutylsulfonyl, 1,2-dimethyl-cyclobutylsulfonyl, 1,3-dimethyl-cyclobutylsulfonyl, 2,2-dimethyl-cyclobutylsulfonyl, 2,3-dimethyl-cyclobutylsulfonyl, 2,4-dimethyl-cyclobutylsulfonyl, 3,3-dimethyl-cyclobutylsulfonyl, 1-n-propyl-cyclopropylsulfonyl, 2-n-propyl-cyclopropylsulfonyl, 1-i-propyl-cyclopropylsulfonyl, 2-i-propyl-cyclopropylsulfonyl, 1,2,2-trimethyl-cyclopropylsulfonyl, 1,2,3-trimethyl-cyclopropylsulfonyl, 2,2,3-trimethyl-cyclopropylsulfonyl, 1-ethyl-2-methyl-cyclopropylsulfonyl, 2-ethyl-1-methyl-cyclopropylsulfonyl, 2-ethyl-2-methyl-cyclopropylsulfonyl, 2-ethyl-3-methyl-cyclopropylsulfonyl and the like.

The industrial antibacterial and antifungal agent, algicide and agent for preventing adhesion of organisms of the present invention may contain the iodopropargylamine compound of the above general formula (1) as the active ingredient.

The preferred compound contained as an active ingredient of the industrial antibacterial and antifungal agent, algicide and agent for preventing adhesion of organisms of the present invention is an iodopropargylamine compound of the formula (1) wherein $R^1$ and $R^2$ each independently represent a hydrogen atom or an alkyl group having by 1 to 3 carbon atoms, or $R^1$ and $R^2$ combine with each other to form a pentamethylene group, $R^3$ represents a hydrogen atom or an alkyl group having 1 to 3 carbon atoms, and X and Y each independently represent a cyano group, an alkoxycarbonyl group having 2 to 4 carbon atoms, an unsubstituted phenylcarbonyl group or an unsubstituted phenyl sulfonyl group.

Preferred examples of the compound are listed in Table 1 below. However, the compound used in the present invention is not limited to these.

Symbols in the table mean the followings;

Me: methyl group, Et: ethyl group, Pr: normal propyl group and isopropyl group, Bu: normal butyl group, isobuty group, secondary butyl group and tertiary butyl group, Pen: normal pentyl group and isomer thereof, Hex: normal hexyl group and isomer thereof, Ph: phenyl group.

—$(CH_2)_4$— or —$(CH_2)_5$— in the table means that $R^1$ and $R^2$ form a saturated 5-membered or 6-membered ring together with a carbon atom bonded thereto.

TABLE 1

(1)

| $R^1$ | $R^2$ | $R^3$ | X | Y |
|---|---|---|---|---|
| H | H | H | $CO_2Me$ | $CO_2Me$ |
| H | H | H | $CO_2Et$ | $CO_2Me$ |
| H | H | H | $CO_2Et$ | $CO_2Et$ |
| H | H | H | $CO_2Pr$ | $CO_2Et$ |
| H | H | H | $CO_2Pr$ | $CO\cdot Pr$ |
| H | H | H | $CO_2Bu$ | $CO_2Et$ |
| H | H | H | $CO_2Bu$ | $CO_2Bu$ |
| H | H | H | $CO_2Pen$ | $CO_2Et$ |
| H | H | H | $CO_2Pen$ | $CO_2Pen$ |
| H | H | H | $CO_2Hex$ | $CO_2Me$ |
| H | H | H | $CO_2Hex$ | $CO_2Hex$ |
| Me | H | H | $CO_2Me$ | $CO_2Me$ |
| Me | H | H | $CO_2Et$ | $CO_2Me$ |
| Me | H | H | $CO_2Et$ | $CO_2Et$ |
| Me | H | H | $CO_2Pr$ | $CO_2Et$ |
| Me | H | H | $CO_2pr$ | $CO_2Pr$ |
| Me | H | H | $CO_2Bu$ | $CO_2Et$ |
| Me | H | H | $CO_2Bu$ | $CO_2Bu$ |
| Me | H | H | $CO_2Pen$ | $CO_2Et$ |
| Me | H | H | $CO_2Pen$ | $CO_2Pen$ |
| Me | H | H | $CO_2Hex$ | $CO_2Me$ |
| Me | H | H | $CO_2Hex$ | $CO_2Hex$ |
| Me | Me | H | $CO_2Me$ | $CO_2Me$ |
| Me | Me | H | $CO_2Et$ | $CO_2Me$ |
| Me | Me | H | $CO_2Et$ | $CO_2Et$ |
| Me | Me | H | $CO_2Pr$ | $CO_2Et$ |
| Me | Me | H | $CO_2Pr$ | $CO_2Pr$ |
| Me | Me | H | $CO_2Bu$ | $CO_2Et$ |
| Me | Me | H | $CO_2Bu$ | $CO_2Bu$ |
| Me | Me | H | $CO_2Pen$ | $CO_2Et$ |
| Me | Me | H | $CO_2Pen$ | $CO_2Pen$ |
| Me | Me | H | $CO_2Hex$ | $CO_2Me$ |
| Me | Me | H | $CO_2Hex$ | $CO_2Hex$ |
| H | H | Me | $CO_2Me$ | $CO_2Me$ |
| H | H | Me | $CO_2Et$ | $CO_2Me$ |
| H | H | Me | $CO_2Et$ | $CO_2Et$ |
| H | H | Me | $CO_2Pr$ | $CO_2Et$ |
| H | H | Me | $CO_2Pr$ | $CO_2Pr$ |
| H | H | Me | $CO_2Bu$ | $CO_2Et$ |
| H | H | Me | $CO_2Bu$ | $CO_2Bu$ |
| H | H | Me | $CO_2Pen$ | $CO_2Et$ |
| H | H | Me | $CO_2Pen$ | $CO_2Pen$ |
| H | H | Me | $CO_2Hex$ | $CO_2Me$ |
| H | H | Me | $CO_2Hex$ | $CO_2Hex$ |
| Me | H | Me | $CO_2Me$ | $CO_2Me$ |
| Me | H | Me | $CO_2Et$ | $CO_2Me$ |
| Me | H | Me | $CO_2Et$ | $CO_2Et$ |
| Me | H | Me | $CO_2Pr$ | $CO_2Et$ |
| Me | H | Me | $CO_2Bu$ | $CO_2Pr$ |
| Me | H | Me | $CO_2Bu$ | $CO_2Et$ |
| Me | H | Me | $CO_2Bu$ | $CO_2Bu$ |
| Me | H | Me | $CO_2Pen$ | $CO_2Et$ |
| Me | H | Me | $CO_2Pen$ | $CO_2Pen$ |
| Me | H | Me | $CO_2Hex$ | $CO_2Me$ |
| Me | H | Me | $CO_2Hex$ | $CO_2Hex$ |
| Me | Me | Me | $CO_2Me$ | $CO_2Me$ |
| Me | Me | Me | $CO_2Et$ | $CO_2Me$ |
| Me | Me | Me | $CO_2Et$ | $CO_2Et$ |
| Me | Me | Me | $CO_2Pr$ | $CO_2Et$ |
| Me | Me | Me | $CO_2Pr$ | $CO_2Pr$ |
| Me | Me | Me | $CO_2Bu$ | $CO_2Et$ |
| Me | Me | Me | $CO_2Bu$ | $CO_2Bu$ |
| Me | Me | Me | $CO_2Pen$ | $CO_2Pen$ |
| Me | Me | Me | $CO_2Pen$ | $CO_2Bu$ |
| Me | Me | Me | $CO_2Hex$ | $CO_2Me$ |
| Me | Me | Me | $CO_2Hex$ | $CO_2Hex$ |
| H | H | Et | $CO_2Me$ | $CO_2Me$ |

TABLE 1-continued

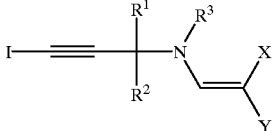

(1)

| R¹ | R² | R³ | X | Y |
|---|---|---|---|---|
| H | H | Et | CO₂Et | CO₂Et |
| H | H | Pr | CO₂Me | CO₂Me |
| H | H | Pr | CO₂Et | CO₂Et |
| Me | H | Et | CO₂Me | CO₂Me |
| Me | H | Et | CO₂Et | CO₂Et |
| Me | H | Pr | CO₂Me | CO₂Me |
| Me | H | Pr | CO₂Et | CO₂Et |
| Me | Me | Et | CO₂Me | CO₂Me |
| Me | Me | Et | CO₂Et | CO₂Et |
| Me | Me | Pr | CO₂Me | CO₂Me |
| Me | Me | Pr | CO₂Et | CO₂Et |
| Et | H | H | CO₂Me | CO₂Me |
| Et | H | H | CO₂Et | CO₂Et |
| Et | H | Me | CO₂Me | CO₂Me |
| Et | H | Me | CO₂Et | CO₂Et |
| Pr | H | H | CO₂Me | CO₂Me |
| Pr | H | H | CO₂Et | CO₂Et |
| Pr | H | Me | CO₂Me | CO₂Me |
| Pr | H | Me | CO₂Et | CO₂Et |
| Et | Me | H | CO₂Me | CO₂Me |
| Et | Me | H | CO₂Et | CO₂Et |
| Et | Me | Me | CO₂Me | CO₂Me |
| Et | Me | Me | CO₂Et | CO₂Et |
| Et | Et | H | CO₂Me | CO₂Me |
| Et | Et | H | CO₂Et | CO₂Et |
| Et | Et | Me | CO₂Me | CO₂Me |
| Pr | Et | Me | CO₂Et | CO₂Et |
| Pr | Me | H | CO₂Me | CO₂Me |
| Pr | Et | R | CO₂Et | CO₂Et |
| Pr | Et | Me | CO₂Me | CO₂Me |
| Pr | Me | Me | CO₂Et | CO₂Et |
| —(CH₂)₄— | | H | CO₂Me | CO₂Me |
| —(CH₂)₄— | | H | CO₂Et | CO₂Et |
| —(CH₂)₄— | | Me | CO₂Me | CO₂Me |
| —(CH₂)₄— | | Me | CO₂Et | CO₂Et |
| —(CH₂)₅— | | H | CO₂Me | CO₂Me |
| —(CH₂)₅— | | H | CO₂Et | CO₂Et |
| —(CH₂)₅— | | Me | CO₂Me | CO₂Me |
| —(CH₂)₅— | | Me | CO₂Et | CO₂Et |
| H | H | H | CN | CO₂Me |
| H | H | H | CN | CO₂Et |
| H | H | H | CN | CO₂Pr |
| H | H | H | CN | CO₂Bu |
| H | H | H | CN | CO₂Pen |
| H | H | H | CN | CO₂Hex |
| Me | H | H | CN | CO₂Me |
| Me | H | H | CN | CO₂Et |
| Me | H | H | CN | CO₂Pr |
| Me | H | R | CN | CO₂Bu |
| Me | H | H | CN | CO₂Pen |
| Me | H | H | CN | CO₂Hex |
| Me | Me | H | CN | CO₂Me |
| Me | Me | H | CN | CO₂Et |
| Me | Me | H | CN | CO₂Pr |
| Me | Me | H | CN | CO₂Bu |
| Me | Me | H | CN | CO₂Pen |
| Me | Me | H | CN | CO₂Hex |
| H | H | Me | CN | CO₂Me |
| H | H | Me | CN | CO₂Et |
| H | H | Me | CN | CO₂Pr |
| H | H | Me | CN | CO₂Bu |
| H | H | Me | CN | CO₂Pen |
| H | H | Me | CN | CO₂Hex |
| Me | H | Me | CN | CO₂Me |
| Me | H | Me | CN | CO₂Et |
| Me | H | Me | CN | Co₂Pr |
| Me | H | Me | CN | CO₂Bu |
| Me | H | Me | CN | CO₂Pen |
| Me | H | Me | CN | CO₂Hex |
| Me | Me | Me | CN | CO₂Me |
| Me | Me | Me | CN | CO₂Et |
| Me | Me | Me | CN | CO₂Pr |
| Me | Me | Me | CN | CO₂Bu |
| Me | Me | Me | CN | CO₂Pen |
| Me | Me | Me | CN | CO₂Hex |
| H | H | Et | CN | CO₂Me |
| H | H | Et | CN | CO₂Et |
| H | H | Pr | CN | CO₂Me |
| H | H | Pr | CN | CO₂Et |
| Me | H | Et | CN | CO₂Me |
| Me | H | Et | CN | CO₂Et |
| Me | H | Pr | CN | CO₂Me |
| Me | H | Pr | CN | CO₂Et |
| Me | Me | Et | CN | CO₂Me |
| Me | Me | Et | CN | CO₂Et |
| Me | Me | Pr | CN | CO₂Me |
| Me | Me | Pr | CN | CO₂Et |
| Et | H | H | CN | CO₂Me |
| Et | H | H | CN | CO₂Et |
| Et | H | Me | CN | CO₂Me |
| Et | H | Me | CN | CO₂Et |
| Pr | H | H | CN | CO₂Me |
| Pr | H | H | CN | CO₂Et |
| Pr | H | Me | CN | CO₂Me |
| Pr | H | Me | CN | CO₂Et |
| Et | Me | H | CN | CO₂Me |
| Et | Me | H | CN | CO₂Et |
| Et | Me | Me | CN | CO₂Me |
| Et | Me | Me | CN | CO₂Et |
| Et | Et | H | CN | CO₂Me |
| Et | Et | H | CN | CO₂Et |
| Et | Et | Me | CN | CO₂Me |
| Et | Et | Me | CN | CO₂Et |
| Pr | Me | H | CN | CO₂Me |
| Pr | Et | H | CN | CO₂Et |
| Pr | Et | Me | CN | CO₂Me |
| Pr | Me | Me | CN | CO₂Et |
| —(CH₂)₄— | | H | CN | CO₂Me |
| —(CH₂)₄— | | H | CN | CO₂Et |
| —(CH₂)₄— | | Me | CN | CO₂Me |
| —(CH₂)₄— | | Me | CN | CO₂Et |
| —(CH₂)₅— | | H | CN | CO₂Me |
| —(CH₂)₅— | | H | CN | CO₂Et |
| —(CH₂)₅— | | Me | CN | CO₂Me |
| —(CH₂)₅— | | Me | CN | CO₂Et |
| H | H | H | CN | CN |
| Me | H | H | CN | CN |
| Me | Me | H | CN | CN |
| H | H | Me | CN | CN |
| Me | H | Me | CN | CN |
| Me | Me | Me | CN | CN |
| H | H | H | CN | CN |
| Me | Me | Me | CN | CN |
| —(CH₂)₄— | | H | CN | CN |
| —(CH₂)₄— | | Me | CN | CN |
| —(CH₂)₅— | | H | CN | CN |
| —(CH₂)₅— | | Me | CN | CN |
| H | H | H | COMe | COMe |
| H | H | H | COEt | COMe |
| H | H | H | COEt | COEt |
| H | H | H | COPr | COEt |
| H | H | H | COPr | COPr |
| H | H | H | COBu | COMe |
| H | H | H | COPen | COEt |

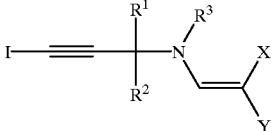

TABLE 1-continued (1)

| R¹ | R² | R³ | X | Y |
|---|---|---|---|---|
| H | H | H | COHex | COMe |
| Me | H | H | COMe | COMe |
| Me | N | H | COEt | COMe |
| Me | H | H | COEt | COEt |
| Me | H | H | COPr | COEt |
| Me | H | H | COPr | COPr |
| Me | H | H | COBu | COMe |
| Me | H | H | COPen | COEt |
| Me | H | H | COHex | COMe |
| Me | Me | H | COMe | COMe |
| Me | Me | H | COEt | COMe |
| Me | Me | H | COEt | COEt |
| Me | Me | H | COPr | COEt |
| Me | Me | H | COPr | COPr |
| Me | Me | H | COBu | COMe |
| Me | Me | H | COPen | COEt |
| Me | Me | H | COHex | CCMe |
| H | H | Me | COMe | COMe |
| H | H | Me | COEt | COMe |
| H | H | Me | COEt | COEt |
| H | H | Me | COPr | COEt |
| H | H | Me | COPr | COPr |
| H | H | Me | COBu | COEt |
| H | H | Me | COPen | COEt |
| H | H | Me | COHex | COMe |
| Me | H | Me | COMe | COMe |
| Me | H | Me | COEt | COMe |
| Me | H | Me | COEt | COEt |
| Me | H | Me | COPr | COEt |
| Me | H | Me | COPr | COPr |
| Me | H | Me | COBu | COEt |
| Me | H | Me | COPen | COEt |
| Me | H | Me | COHex | COMe |
| Me | Me | Me | COMe | COMe |
| Me | Me | Me | COEt | COMe |
| Me | Me | Me | COEt | COEt |
| Me | Me | Me | COPr | COEt |
| Me | Me | Me | COPr | COPr |
| Me | Me | Me | COBu | COEt |
| Me | Me | Me | COPen | COEt |
| Me | Me | Me | COHex | COMe |
| H | H | H | CN | COMe |
| H | H | H | CN | COEt |
| H | H | H | CN | COPr |
| H | H | H | CN | COBu |
| H | H | H | CN | COPen |
| H | H | H | CN | COHex |
| Me | H | H | CN | COMe |
| Me | H | H | CN | COEt |
| Me | H | H | CN | COPr |
| Me | H | H | CN | COBu |
| Me | H | H | CN | COPen |
| Me | H | H | CN | COHex |
| Me | Me | H | CN | COMe |
| Me | Me | H | CN | COEt |
| Me | Me | H | CN | COPr |
| Me | Me | H | CN | COBu |
| Me | Me | H | CN | COPen |
| Me | Me | H | CN | COHex |
| H | H | Me | CN | COMe |
| H | H | Me | CN | COEt |
| H | H | Me | CN | COPr |
| H | H | Me | CN | COBu |
| H | H | Me | CN | COPen |
| R | H | Me | CN | COHex |
| Me | H | Me | CN | COMe |
| Me | H | Me | CN | COEt |
| Me | H | Me | CN | COPr |
| Me | H | Me | CN | COBu |
| Me | H | Me | CN | COPen |
| Me | H | Me | CN | COHex |
| Me | Me | Me | CN | COMe |
| Me | Me | Me | CN | COEt |
| Me | Me | Me | CN | COPr |
| Me | Me | Me | CN | COBu |
| Me | Me | Me | CN | COPen |
| Me | Me | Me | CN | COHex |
| —(CH$_2$)$_4$— | | H | CN | COMe |
| —(CH$_2$)$_4$— | | H | CN | COEt |
| —(CH$_2$)$_4$— | | Me | CN | COMe |
| —(CH$_2$)$_4$— | | Me | CN | COEt |
| —(CH$_2$)$_5$— | | H | CN | COMe |
| —(CH$_2$)$_5$— | | H | CN | COEt |
| —(CH$_2$)$_5$— | | Me | CN | COMe |
| —(CH$_2$)$_5$— | | Me | CN | COEt |
| H | H | H | COMe | CO$_2$Me |
| H | H | H | COMe | CO$_2$Et |
| H | H | H | COMe | CO$_2$Pr |
| H | H | H | COMe | CO$_2$Bu |
| H | H | H | COMe | CO$_2$Pen |
| H | H | H | COMe | CO$_2$Hex |
| H | H | H | COEt | CO$_2$Me |
| H | H | H | COPr | CO$_2$Et |
| H | H | H | COBu | CO$_2$Et |
| H | H | H | COPen | CO$_2$Et |
| H | H | H | COHex | CO$_2$Me |
| Me | H | H | COMe | CO$_2$Me |
| Me | H | H | COMe | CO$_2$Et |
| Me | H | H | COMe | CO$_2$Pr |
| Me | H | H | COMe | CO$_2$Bu |
| Me | H | H | COMe | CO$_2$Pen |
| Me | H | H | COMe | CO$_2$Hex |
| Me | H | H | COEt | CO$_2$Me |
| Me | H | H | COPr | CO$_2$Et |
| Me | H | H | COBu | CO$_2$Et |
| Me | H | H | COPen | CO$_2$Et |
| Me | H | H | COHex | CO$_2$Me |
| Me | Me | H | COMe | Co$_2$Me |
| Me | Me | H | COMe | CO$_2$Et |
| Me | Me | H | COMe | CO$_2$Pr |
| Me | Me | H | COMe | CO$_2$Bu |
| Me | Me | H | COMe | CO$_2$Pen |
| Me | Me | H | COMe | CO$_2$Hex |
| Me | Me | H | COEt | CO$_2$Me |
| Me | Me | H | COEt | CO$_2$Et |
| Me | Me | H | COPr | CO$_2$Et |
| Me | Me | H | COBu | CO$_2$Et |
| Me | Me | H | COPen | CO$_2$Et |
| Me | Me | H | COHex | CO$_2$Me |
| H | H | Me | COMe | CO$_2$Me |
| H | H | Me | COMe | CO$_2$Et |
| H | H | Me | COMe | CO$_2$Pr |
| Me | H | Me | COMe | CO$_2$Me |
| Me | H | Me | COMe | CO$_2$Et |
| Me | H | Me | COMe | CO$_2$Pr |
| Me | Me | Me | COMe | CO$_2$Me |
| Me | Me | Me | COMe | CO$_2$Et |
| Me | Me | Me | COMe | CO$_2$Pr |
| —(CH$_2$)$_4$— | | H | COMe | CO$_2$Me |
| —(CH$_2$)$_4$— | | H | COMe | CO$_2$Et |
| —(CH$_2$)$_4$— | | Me | COMe | CO$_2$Me |
| —(CH$_2$)$_4$— | | Me | COMe | CO$_2$Et |
| —(CH$_2$)$_5$— | | H | COMe | CO$_2$Me |
| —(CH$_2$)$_5$— | | H | COMe | CO$_2$Et |

TABLE 1-continued

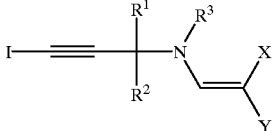

(1)

| R¹ | R² | R³ | X | Y |
|---|---|---|---|---|
| —(CH₂)₅— | | Me | COMe | CO₂Me |
| —(CH₂)₅— | | Me | COMe | CO₂Et |
| H | H | H | SO₂Me | CO₂Me |
| H | H | H | SO₂Me | CO₂Et |
| H | H | H | SO₂Me | CO₂Pr |
| H | H | H | SO₂Me | CO₂Bu |
| H | H | H | SO₂Me | CO₂Pen |
| H | H | H | SO₂Me | CO₂Hex |
| H | H | H | SO₂Et | CO₂Et |
| H | H | H | SO₂Pr | CO₂Et |
| H | H | H | SO₂Bu | CO₂Et |
| H | H | H | SO₂Pen | CO₂Et |
| H | H | H | SO₂Hex | CO₂Et |
| Me | H | H | SO₂Me | CO₂Me |
| Me | H | H | SO₂Me | CO₂Et |
| Me | H | H | SO₂Me | CO₂Pr |
| Me | Me | H | SO₂Me | CO₂Me |
| Me | Me | H | SO₂Me | CO₂Et |
| Me | Me | H | SO₂Me | CO₂Pr |
| H | H | Me | SO₂Me | CO₂Me |
| H | H | Me | SO₂Me | CO₂Et |
| H | H | Me | SO₂Me | CO₂Pr |
| Me | H | Me | SO₂Me | Co₂Me |
| Me | H | Me | SO₂Me | CO₂Et |
| Me | Me | Me | SO₂Me | CO₂Me |
| Me | Me | Me | SO₂Me | CO₂Et |
| —(CH₂)₄— | | H | SO₂Me | CO₂Me |
| —(CH₂)₄— | | H | SO₂Me | CO₂Et |
| —(CH₂)₄— | | Me | SO₂Me | CO₂Me |
| —(CH₂)₄— | | Me | SO₂Me | CO₂Et |
| —(CH₂)₅— | | H | SO₂Me | CO₂Me |
| —(CH₂)₅— | | H | SO₂Me | CO₂Et |
| —(CH₂)₅— | | Me | SO₂Me | CO₂Me |
| —(CH₂)₅— | | Me | SO₂Me | CO₂Et |
| H | H | H | SO₂Me | COMe |
| H | H | H | SO₂Me | COEt |
| H | H | H | SO₂Et | COMe |
| H | H | H | SO₂Et | COEt |
| Me | H | H | SO₂Me | COMe |
| Me | H | H | SO₂Me | COMe |
| Me | H | H | SO₂Et | COMe |
| Me | H | H | SO₂Et | COEt |
| Me | Me | H | SO₂Me | COMe |
| Me | Me | H | SO₂Me | COEt |
| Me | Me | H | SO₂Et | COMe |
| Me | Me | H | SO₂Et | COEt |
| H | H | Me | SO₂Me | COMe |
| H | H | Me | SO₂Me | COEt |
| Me | H | Me | SO₂Me | COMe |
| Me | H | Me | SO₂Me | COEt |
| Me | Me | Me | SO₂Me | COMe |
| Me | Me | Me | SO₂Me | COEt |
| —(CH₂)₄— | | H | SO₂Me | COMe |
| —(CH₂)₄— | | Me | SO₂Me | COEt |
| —(CH₂)₄— | | Me | SO₂Me | COPr |
| —(CH₂)₅— | | H | SO₂Me | COMe |
| —(CH₂)₅— | | Me | SO₂Me | COEt |
| —(CH₂)₅— | | Me | SO₂Me | COPr |
| H | H | H | SO₂Me | CN |
| H | H | H | SO₂Et | CN |
| H | H | H | SO₂Pr | CN |
| H | H | H | SO₂Bu | CN |
| H | H | H | SO₂Pen | CN |
| H | H | H | SO₂Hex | CN |
| Me | H | H | SO₂Me | CN |
| Me | H | H | SO₂Et | CN |
| Me | H | H | SO₂Pr | CN |

TABLE 1-continued

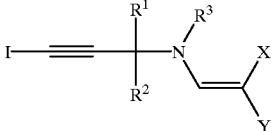

(1)

| R¹ | R² | R³ | X | Y |
|---|---|---|---|---|
| Me | H | H | SO₂Bu | CN |
| Me | H | H | SO₂Pen | CN |
| Me | H | H | SO₂Hex | CN |
| Me | Me | H | SO₂Me | CN |
| Me | Me | H | SO₂Et | CN |
| Me | Me | H | SO₂Pr | CN |
| Me | Me | H | SO₂Bu | CN |
| Me | Me | H | SO₂Pen | CN |
| Me | Me | H | SO₂Hex | CN |
| H | H | Me | SO₂Me | CN |
| H | H | Me | SO₂Et | CN |
| H | H | Me | SO₂Pr | CN |
| H | H | Me | SO₂Bu | CN |
| H | H | Me | SO₂Pen | CN |
| H | H | Me | SO₂Hex | CN |
| Me | H | Me | SO₂Me | CN |
| Me | H | Me | SO₂Et | CN |
| Me | H | Me | SO₂Pr | CN |
| Me | H | Me | SO₂Bu | CN |
| Me | H | Me | SO₂Pen | CN |
| Me | H | Me | SO₂Hex | CN |
| Me | Me | Me | SO₂Me | CN |
| Me | Me | Me | SO₂Et | CN |
| Me | Me | Me | SO₂Pr | CN |
| Me | Me | Me | SO₂Bu | CN |
| Me | Me | Me | SO₂Pen | CN |
| Me | Me | Me | SO₂Hex | CN |
| H | H | Et | SO₂Me | CN |
| H | H | Et | SO₂Et | CN |
| H | H | Pr | SO₂Me | CN |
| H | H | Pr | SO₂Et | CN |
| Me | H | Et | SO₂Me | CN |
| Me | H | Et | SO₂Et | CN |
| Me | H | Pr | SO₂Me | CN |
| Me | H | Pr | SO₂Et | CN |
| Me | Me | Et | SO₂Me | CN |
| Me | Me | Et | SO₂Et | CN |
| Me | Me | Pr | SO₂Me | CN |
| Me | Me | Pr | SO₂Et | CN |
| Et | H | H | SO₂Me | CN |
| Et | H | H | SO₂Et | CN |
| Et | H | Me | SO₂Me | CN |
| Et | H | Me | SO₂Et | CN |
| Pr | H | H | SO₂Me | CN |
| Pr | H | H | SO₂Et | CN |
| Pr | H | Me | SO₂Me | CN |
| Pr | H | Me | SO₂Et | CN |
| Et | Me | H | SO₂Me | CN |
| Et | Me | H | SO₂Et | CN |
| Et | Me | Me | SO₂Me | CN |
| Et | Me | Me | SO₂Et | CN |
| Et | Et | H | SO₂Me | CN |
| Et | Et | H | SO₂Et | CN |
| Et | Et | Me | SO₂Bu | CN |
| Et | Et | Me | SO₂Et | CN |
| Pr | Me | H | SO₂Me | CN |
| Pr | Et | H | SO₂Et | CN |
| Pr | Et | Me | SO₂Me | CN |
| Pr | Me | Me | SO₂Et | CN |
| —(CH₂)₄— | | H | SO₂Me | CN |
| —(CH₂)₄— | | H | SO₂Et | CN |
| —(CH₂)₄— | | Me | SO₂Me | CN |
| —(CH₂)₄— | | Me | SO₂Et | CN |
| —(CH₂)₅— | | H | SO₂Me | CN |
| —(CH₂)₅— | | H | SO₂Et | CN |
| —(CH₂)₅— | | Me | SO₂Me | CN |
| —(CH₂)₅— | | Me | SO₂Et | CN |

TABLE 1-continued

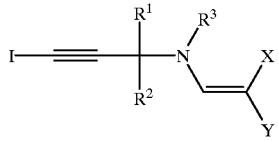

(1)

| R¹ | R² | R³ | X | Y |
|---|---|---|---|---|
| H | H | H | COPh | CO₂Me |
| H | H | H | COPh | CO₂Et |
| H | H | H | COPh | CO₂Pr |
| H | H | H | COPh | CO₂Bu |
| H | H | H | COPh | CO₂Pen |
| H | H | H | COPh | CO₂Hex |
| Me | H | H | COPh | CO₂Me |
| Me | H | R | COPh | CO₂Et |
| Me | H | H | COPh | CO₂Pr |
| Me | Me | H | COPh | CO₂Me |
| Me | Me | H | COPh | CO₂Et |
| Me | Me | H | COPh | CO₂Pr |
| H | H | Me | COPh | CO₂Me |
| H | H | Me | COPh | CO₂Et |
| H | H | Me | COPh | CO₂Pr |
| Me | H | Me | COPh | CO₂Me |
| Me | H | Me | COPh | CO₂Et |
| Me | H | Me | COPh | CO₂Pr |
| Me | Me | Me | COPh | CO₂Me |
| Me | Me | Me | COPh | CO₂Et |
| Me | Me | Me | COPh | CO₂Pr |
| —(CH₂)₄— | | H | COPh | CO₂Me |
| —(CH₂)₄— | | H | COPh | CO₂Et |
| —(CH₂)₄— | | Me | COPh | CO₂Me |
| —(CH₂)₄— | | Me | COPh | CO₂Et |
| —(CH₂)₅— | | H | COPh | CO₂Me |
| —(CH₂)₅— | | H | COPh | CO₂Et |
| —(CH₂)₅— | | Me | COPh | CO₂Me |
| —(CH₂)₅— | | Me | COPh | CO₂Et |
| H | H | H | COPh-2-F | CO₂Me |
| H | H | H | COPh-2-Cl | CO₂Me |
| H | H | H | COPh-4-Cl | CO₂Me |
| H | H | H | COPh-3-Br | CO₂Me |
| H | H | H | COPh-4-I | CO₂Me |
| H | H | H | COPh-4-Me | CO₂Me |
| H | H | H | COPh-2-Et | CO₂Me |
| H | H | H | COPh-3-Pr | CO₂Me |
| H | R | H | COPh-3-OMe | CO₂Me |
| H | H | H | COPh-2-OEt | CO₂Me |
| H | H | H | COPh-4-OPr | CO₂Me |
| H | H | R | COPh-2-NO₂ | CO₂Me |
| H | H | H | COPh-3-CF₃ | CO₂Me |
| Me | Me | H | COPh-2-F | CO₂Me |
| Me | Me | H | COPh-2-Cl | CO₂Me |
| Me | Me | H | COPh-4-Cl | CO₂Me |
| Me | Me | H | COPh-3-Br | CO₂Me |
| Me | Me | H | COPh-4-I | CO₂Me |
| Me | Me | H | COPh-4-Me | CO₂Me |
| Me | Me | H | COPh-2-Et | CO₂Me |
| Me | Me | H | COPh-3-Pr | CO₂Me |
| Me | Me | H | COPh-3-OMe | CO₂Me |
| Me | Me | H | COPh-2-OEt | CO₂Me |
| Me | Me | H | COPh-4-OPr | CO₂Me |
| Me | Me | H | COPh-2-No₂ | CO₂Me |
| Me | Me | H | COPh-3-CF₃ | CO₂Me |
| H | H | H | COPh | CN |
| Me | H | H | COPh | CN |
| Me | Me | H | COPh | CN |
| H | H | Me | COPh | CN |
| Me | H | Me | COPh | CN |
| Me | Me | Me | COPh | CN |
| —(CH₂)₄— | | H | COPh | CN |
| —(CH₂)₄— | | H | COPh | CN |
| H | H | H | COPh-2-F | CN |
| H | H | H | COPh-2-Cl | CN |
| H | H | H | COPh-4-Cl | CN |
| H | H | H | COPh-3-Br | CN |
| H | H | H | COPh-4-I | CN |
| H | H | H | COPh-4-Me | CN |
| H | H | H | COPh-2-Et | CN |
| H | H | H | COPh-3-Pr | CN |
| R | H | H | COPh-3-OMe | CN |
| H | H | H | COPh-2-OEt | CN |
| H | H | H | COPh-3-OPr | CN |
| H | H | H | COPh-2-NO₂ | CN |
| H | H | H | COPh-3-CF₃ | CN |
| Me | Me | H | COPh-2-F | CN |
| Me | Me | H | COPh-2-Cl | CN |
| Me | Me | H | COPh-4-C1 | CN |
| Me | Me | H | COPh-3-Br | CN |
| Me | Me | H | COPh-4-I | CN |
| Me | Me | H | COPh-4-Me | CN |
| Me | Me | H | COPh-2-Et | CN |
| Me | Me | H | COPh-3-Pr | CN |
| Me | Me | H | COPh-3-OMe | CN |
| Me | Me | H | COPh-2-OEt | CN |
| Me | Me | H | COPh-3-OPr | CN |
| Me | Me | H | COPh-2-NO₂ | CN |
| Me | Me | H | COPh-3-CF₃ | CN |
| H | H | H | COPh | COMe |
| H | H | H | COPh | COEt |
| H | H | H | COPh | COPr |
| H | H | H | COPh | COBu |
| H | H | H | COPh | COPen |
| H | H | H | COPh | COHex |
| Me | Me | H | COPh | COMe |
| Me | Me | H | COPh | COEt |
| Me | Me | H | COPh | COPr |
| Me | Me | Me | COPh | COMe |
| Me | Me | Me | COPh | COEt |
| Me | Me | Me | COPh | COPr |
| —(CH₂)₄— | | H | COPh | COMe |
| —(CH₂)₄— | | H | COPh | COEt |
| —(CH₂)₄— | | Me | COPh | COMe |
| —(CH₂)₄— | | Me | COPh | COEt |
| —(CH₂)₅— | | H | COPh | COMe |
| —(CH₂)₅— | | H | COPh | COEt |
| —(CH₂)₅— | | Me | COPh | COMe |
| —(CH₂)₅— | | Me | COPh | COEt |
| H | H | H | COPh | SO₂Me |
| H | H | H | COPh | SO₂Et |
| H | H | H | COPh | SO₂Pr |
| H | H | R | COPh | SO₂Bu |
| H | H | H | COPh | SO₂Pen |
| H | H | H | COPh | SO₂Hex |
| Me | Me | H | COPh | SO₂Me |
| Me | Me | H | COPh | SO₂Et |
| Me | Me | H | COPh | SO₂Pr |
| Me | Me | Me | COPh | SO₂Me |
| Me | Me | Me | COPh | SO₂Et |
| Me | Me | Me | COPh | SO₂Pr |
| —(CH₂)₄— | | H | COPh | SO₂Me |
| —(CH₂)₄— | | H | COPh | SO₂Et |
| —(CH₂)₄— | | Me | COPh | SO₂Me |
| —(CH₂)₄— | | Me | COPh | SO₂Et |
| —(CH₂)₅— | | H | COPh | SO₂Me |
| —(CH₂)₅— | | H | COPh | SO₂Et |
| —(CH₂)₅— | | Me | COPh | SO₂Me |
| —(CH₂)₅— | | Me | COPh | SO₂Et |
| H | H | H | SO₂Ph | CN |
| Me | H | H | SO₂Ph | CN |
| Me | Me | H | SO₂Ph | CN |
| H | H | Me | SO₂Ph | CN |
| Me | H | Me | SO₂Ph | CN |

TABLE 1-continued

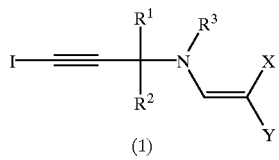

(1)

| R¹ | R² | R³ | X | Y |
|---|---|---|---|---|
| Me | Me | Me | SO₂Ph | CN |
| —(CH₂)₄— | | H | SO₂Ph | CN |
| —(CH₂)₅— | | H | SO₂Ph | CN |
| H | H | H | SO₂Ph-2-F | CN |
| H | H | H | SO₂Ph-2-Cl | CN |
| H | H | H | SO₂Ph-4-Cl | CN |
| H | H | H | SO₂Ph-3-Br | CN |
| H | H | H | SO₂Ph-4-I | CN |
| H | H | H | SO₂Ph-4-Me | CN |
| H | H | H | SO₂Ph-2-Et | CN |
| H | H | H | SO₂Ph-3-Pr | CN |
| H | H | H | SO₂Ph-3-OMe | CN |
| H | H | H | SO₂Ph-2-OEt | CN |
| H | H | H | SO₂Ph-4-OPr | CN |
| H | H | H | SO₂Ph-2-NO₂ | CN |
| H | H | H | SO₂Ph-3-CF₃ | CN |
| Me | Me | H | SO₂Ph-2-F | CN |
| Me | Me | H | SO₂Ph-2-Cl | CN |
| Me | Me | H | SO₂Ph-4-Cl | CN |
| Me | Me | H | SO₂Ph-3-Br | CN |
| Me | Me | H | SO₂Ph-4-I | CN |
| Me | Me | H | SO₂Ph-4-Me | CN |
| Me | Me | H | SO₂Ph-2-Et | CN |
| Me | Me | H | SO₂Ph-3-Pr | CN |
| Me | Me | H | SO₂Ph-3-OMe | CN |
| Me | Me | H | SO₂Ph-2-OEt | CN |
| Me | Me | H | SO₂Ph-4-OPr | CN |
| Me | Me | H | SO₂Ph-2-NO₂ | CN |
| Me | Me | H | SO₂Ph-3-CF₃ | CN |

The iodopropargyl amine compound of the present invention can be easily synthesized by the following method.

$R^1$, $R^2$, $R^3$, X and Y in the following reaction formula are the same as defined above and R represents an alkyl group having 1 to 3 carbon atoms.

Step A

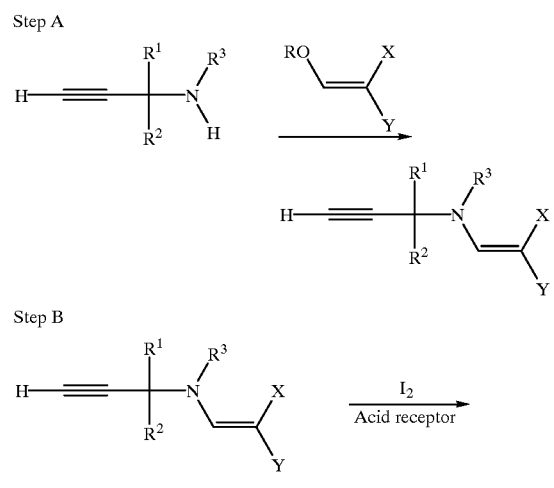

Step B

In the step A, the propargylenamine compound can be easily synthesized by mixing and stirring a propargylamine compound with alkoxymethylene compound in an alcohol solvent such as methanol or ethanol.

The reaction temperature is generally −30 to 150° C., preferably 0 to 50° C.

The reaction generally completes in 0.5 to 24 hours.

In the step B, the iodopropargylamine compound can be easily synthesized by reacting a propargylenamine compound with simple iodine as an iodinating agent in the presence of an acid receptor such as a hydroxide, carbonate, bicarbonate or hydride of an alkali metal, or hydroxide or carbonate of an alkali earth metal, preferably sodium hydroxide or potassium hydroxide in an alcohol solvent such as methanol or ethanol.

The reaction temperature is generally −30 to 100° C., preferably −10 to 50° C.

The iodinating reaction generally completes in 0.5 to 24 hours.

The target compounds obtained by the above method can be made into a pure product through purification by recrystallization with an appropriate solvent or by column chromatography, etc.

The iodopropargylamine compound of the present invention may be used alone as an active ingredient. Alternatively, when the industrial antibacterial and antifungal agent, algicide or agent for preventing adhesion of organisms of the present invention are used, they may be used as mixed agent by further adding thereto one or more known industrial antibacterial and antifungal agent, algicide or agent for preventing adhesion of organisms.

Typical examples of them are given below, however, they are not limited to these; cuprous oxide, quaternary ammonium compounds, allylisothiocyanate, 2-amino-3-chloro-1,4-naphthoquinone, ethylene-bis-thiocyanate, 2-n-octyl-3-isothiazolone, glutaraldehyde, 5-chloro-2-n-decyl-3-isothiazolone, 5-chloro-2,4-difluoro-6-methoxyisophthalonitrile, 2-chloro-4-methylamino-6-isopropylamino-s-triazine, 5-chloro-2-methyl-3-isothiazolone, 2,3-dichloro-1,4-naphthoquinone, diiodomethyl-p-tolylsulfone, N,N-dimethyl-N'-phenyl-N'-(fluorodichloromethylthio)sulfamide, N-(3,4-dichlorophenyl)-N'-methylurea, N,N-dimethyl-N'-(3,4-dichlorophenyl)urea, zinc dimethyldithiocarbamate, 2,6-dichloro-3,5-dicyano-4-phenylpyridine, 2,4-dichloro-6-(o-chloroanilino)-s-triazine, 4,5-dichloro-2-(4-chlorobenzyl)-3-isothiazolone, 4,5-dichloro-2-(4-chlorophenyl)-3-isothiazolone, 4,5-dichloro-2-n-hexyl-3-isothiazolone, 4,5-dichloro-2-n-octyl-3-isothiazolone, 1,2-dibromo-2,4-dicyanobutane, 2,2-dibromo-3-nitrilopropionamide, 2-thiocyanomethylthiobenzothiazole, 2-(4-thiazolyl) benzimidazole, thiabendazole, tetrafluoroisophthalonitrile, 2,3,5,6-tetrachloro-4-(methylfulfonyl)pyridine, tetraphenyl borane pyridine salts, tetramethylthiuramdisulfide, tetraethylthiuramdisulfide, tetraisopropylthiuramdisulfide, tetra-n-butylthiuramdisulfide, tetrachloroisophthalonitrile, tetrachlorophthalonitrile, Cu-10% Ni solid-solution alloy, N-treichloromethylthiotetrahydrophthalimide, N-trichloromethylthiophthalimide, 2,3,6-trichloro-4- propylsulfonylpyridine, N-(2,4,6-trichlorophenyl) maleimide, 4,5-trimethylene-2-methyl-3-isothiazolone, 2-pyridinethiol-1-oxide zinc salts, 2,3,3-triiodoallylalcohol, N-(fluorodichloromethylthio)phthalimide, bis-dimethyldithiocarbamoyl zince ethylene-bis-dithiocarbamate, N-phenethyldichloromaleimide, 2-bromo-2-nitropropanediol, 5-bromo-5-nitro-1,3-dioxane, bromochlorodimethylhydantoin, N-benzyldichloromaleimide, 1,2-benzisothiazolin-3-one, 2-(methoxycarbonylamino)benzimidazole, 4-methyl-5-chloro-2-n-octyl-3-isothiazolone, 2-methylthio-4-t-butylamino-6-cyclopropylamino-s-triazine, N-2-methyl-6-ethylphenyldichloromaleimide, 2-methyl-3-isothiazolone, methylene-bis-thiocyanate, N-3-iodo-2-propynyl-O-butylcarbamate, O-3-iodo-2-propynyl-N-butylcarbamate.

Further, the iodopropargylamine compound used as an active ingredient in the present invention may be a single compound or a mixture of several kinds of iodopropargylamine compounds.

The iodopropargylamine compound used as an active ingredient in the present invention may be added alone to a system of the above application purpose. They may also be formulated in a mixture of an active ingredient and an appropriate carrier or solvent as required, or in an aqueous emulsion or dispersion.

When the formulations of the industrial antibacterial and antifungal agent, algicide and agent for preventing adhesion of organisms of the present invention are given an outline in the application field of industrial antibacterial and antifungal agents and algicides, the iodopropargylamine compound used as an active ingredient in the present invention is mixed with appropriate carriers and additives, for example, a surfactant, binder and stabilizer etc., and formulated into wettable powder, emulsifiable concentrate, sol (flowable) formulation and other appropriate formulations by commonly used methods.

In the case of the preparation of these formulations, the iodopropargylamine compound as an active ingredient has no upper limit of concentration as far as wettable powder, emulsifiable concentrate, liquid formulation, sol formulation and other appropriate formulations can be prepared. However, the iodopropargylamine compound is generally contained in an amount of 1 to 90 wt %, preferably 3 to 40 wt % based on the weight of the formulations.

The carrier which can be used are either one of solid and liquid, which are commonly used in industrial antibacterial and antifungal agents and algicides, and is not limited to a particular kind.

Examples of the solid carrier include mineral powders such as kaolin, bentonite, clay, montmorillonite, diatomaceous earth, mica, vermiculite, gypsum, calcium carbonate, phosphorus lime, white carbon, slaked lime, quartz sand, ammonium sulfate and urea, plant powders such as soybean meal, starch, crystalline celluloses, alumina, silicates, sugar polymers, highly dispersible silicic acids and waxes.

Examples of the liquid carrier include water, alcohol such as methyl alcohol, ethyl alcohol, n-propyl alcohol, isopropyl alcohol, ethyleneglycol and benzyl alcohol, aromatic hydrocarbons such as benzene, toluene, xylene, ethylbenzene, chlorobenzene, cumene and methylnaphthalene, halogenated hydrocarbons such as chloroform, dichloromethane and ethylenedichloride, ethers such as ethylether, dioxane and tetrahydrofuran, ketones such as acetone, methylethylketone, cyclohexanone and methylisobutylketone, esters such as ethylacetate, butylacetate, ethyleneglycolacetate and amylacetate, nitriles such as acetonitrile, propionitrile and acrylonitrile, sulfoxides such as dimethylsulfoxide, alcoholethers such as ethyleneglycolmonomethylether and ethyleneglycol monoethylether, amines such as triethylamine, aliphatic and alicyclic hydrocarbons such as n-hexane and cyclohexane and the like, and further industrial gasoline (petroleum ether, solvent naphtha, etc.), petroleum fractions (paraffin, kerosene, light oil, etc.) and the like.

In the case of formulation of an emulsifiable concentrate, a wettable powder and a sol (flowable) formulation and so on, a surfactant is blended for emulsifying, dispersing, solubilizing, wetting, foaming or spreading it. Examples of the surfactant are given below but it is not limited to these.

Examples of nonionic surfactants include polyoxyethylene alkyl ethers, polyoxyethylene alkyl esters, polyoxyethylene sorbitan alkyl esters and sorbitan alkyl esters.

Examples of anionic surfactants include alkyl benzene sulfonates, alkylsulfosuccinates, alkylsulfates, polyoxyethylene alkylsulfates, aryl sulfonates and lauryl sulfates.

Examples of cationic surfactants include alkylamines (lauryl amine, stearyl trimethylammonium chloride, alkyl dimethylbenzylammonium chloride, etc.).

Examples of ampholytic surfactants include carboxylic acid (betaine type) sulfuric acid esters.

Besides these, a thickener such as polyvinyl alcohol (PVA), carboxylmethyl cellulose (CMC), arabian rubber, polyvinyl acetate, gelatin, casein, sodium alginate, tragacanth gum, guargum, xanthane gum and hydroxypropyl celllose and various additives may be blended.

If necessary, a stabilizer such as an antioxidant or ultraviolet absorber may be further added in an appropriate amount.

The industrial antibacterial and antifungal agent and algicide containing an iodopropargylamine compound of the present invention as an active ingredient can be used for the following purposes:

inhibition of growth of bacteria, fungi and algae in emulsion products such as water paints, adhesives, latexes and acryls, slurry products such as starch, pigments and calcium carbonate and joint cement; preservation of wood in construction materials (for building construction materials and civil engineering construction materials); antisepsis of cutting oil; fungusproofing of surfactants; sterilization and prevention of formation of slime in the cooling towers of the production equipment of plants and building air conditioning systems and in pulp and paper plants; anitbacterial and antifungal treatments of fibers, fabrics and leathers by spraying or immersing; protection from the attack of microbes, fungi and algae to coating films, particularly coating films of exterior coatings during which are exposed to the weather; protection from bacteria, fungi and algae of interior and exterior materials (for housings and medical facilities), building materials (for construction and civil engineering materials, etc.), home electric appliances, domestic sundries and sport goods, which are made from resins such as vinylchloride, polyurethane, polyethylene, polypropylene, silicon, modified silicon, nylon, epoxy and the like; prevention of accumulation of slime in cane and best sugar production equipment; prevention of accumulation of microbes in air washers, scrubber systems and industrial fresh water supply systems; maintenance of sanitary environment at food plants and the like; deodorization and sterilization for washing production equipment, sewage treatment plants and night soil treatment plants; prevention of pollution and accumulation of microbes in petroleum well cutting oil, muddy water and secondary oil recovery process; prevention of growth of bacteria and fungi in paper coating materials and coatings thereof; prevention of pollution by microbes of cosmetics and toiletry products; inhibition of growth of algae in swimming pools and the like; prevention of pollution by microbes of agricultural blends, electrodeposition systems, diagnostic and pharmaceutical products, medical equipment and the like; and prevention of accumulation of microbes in photographic treatments.

The agent for preventing adhesion of organisms containing an iodopropargylamine compound as an active ingredient can be used to prevent the adhesion of harmful aquatic organisms such as shellfishes exemplified by blue mussel (*Mytilus edulis*), barnacle (*Balanus sp.* ), oyster, Hydrozoa, hydra (*Hydra sp.*), serpula (*Serpula sp.*), ascidian, bryzoan and pondsnail, and algae exemplified by *Ulva pertusa, Enteromorpha intestinalis* and *Spirogyra arcta* to fishing nets, bottoms of ships, equipment placed in the sea such as buoys, marine constructions, condensers of cooling water systems at thermal or atomic power plants, inlet channels of cooling water for heat exchangers of the chemical industry, under water constructions such as equipment attached to dam, reservoirs and the like.

Examples of formulation in the case that the iodopropargylamine compound of the present invention is used as an industrial antibacterial and antifungal agent and algicide are given below. The proportions of active ingredients and the types and amounts of carriers and additives are not limited to these.

Formulation example 1 (emulsifiable concentrate)

| Components | wt % |
|---|---|
| Compound of formula (1) | 5 |
| Dimethyl sulfoxide | 85 |
| Methyl isobutyl ketone | 5 |
| Sorpol 800A (emulsifying agent of Toho Kagaku Co.) | 5 |
| | 100 |

An emulsifiable concentrate containing 5% of active ingredient was obtained by mixing and melting the above ingredients.

Formulation example 2 (wettable powder)

| Components | wt % |
|---|---|
| Compound of formula (1) | 20 |
| Lauryl sulfate | 7 |
| Clay | 73 |
| | 100 |

Wettable powder containing 20% of active ingredient was obtained by mixing and milling the above ingredients uniformly.

Formulation example 3 (flowable formulation)

| Components | wt % |
|---|---|
| Compound of formula (1) | 20 |
| Lauryl sulfate | 2 |
| Xanthane gum | 2 |
| Hydroxypropyl cellulose | 1 |
| Distilled water | 75 |
| | 100 |

A flowable formulation containing 20% of active ingredient was obtained by placing the above ingredients in a ball mill to mill and mix for 12 hours.

The formulated industrial antibacterial and antifungal agent and algicide of the present invention may be used in accordance with methods of use of industrial antibacterial and antifungal agent and algicide which have been generally performed, including that formulations are added to and mixed with various industrial raw materials or products directly or after they are diluted with water or an appropriate organic solvent, that they are applied or sprayed onto the surfaces of various industrial raw materials and products, or that industrial raw materials and products are immersed in a diluted solution of the industrial antibacterial and antifungal agent and algicide of the present invention. However, they are not limited to these specific methods.

When the formulations of the industrial antibacterial and antifungal agent, algicide and agent for preventing adhesion of organisms of the present invention are out lined in the application field of agents for preventing adhesion of organisms, the iodopropargylamine compound used as an active ingredient in the present invention may be prepared in the form of a paint, solution, emulsion and so on.

General formulation can be employed for the preparation of the paint, solution, emulsion and so on.

When the agent for preventing adhesion of organisms of the present invention is used in the form of an anti fouling paint, adhesion and propagation of aquatic organisms can be avoided by, for example, mixing a iodopropargylamine compound as an active ingredient and a film forming ingredient to prepare a paint and then applying it to bottoms of ships, marine constructions, intake channels for cooling, underwater constructions and the like.

Oil varnish, synthetic resins, artificial rubber and the like are used as the film forming ingredients.

A solvent, pigment and the like may be further used as required.

In the case of preparation of paint, the iodopropargylamine compound as an active ingredient has no upper limit of concentration as far as it can form a coating film. However, it is used in an amount of 1 to 50 wt %, preferably 5 to 20 wt % based on the weight of the antifouling coating.

Examples of formulation in the case that the agent for preventing adhesion of organisms of the present invention is used as an antifouling paint are given below; however, it is not limited to these.

| Components | wt % |
|---|---|
| Formulation example 4 | |
| Compound of formula (1) | 8 |
| VYHH (vinyl-based synthetic resin of UCC Co.) | 7 |

-continued

| Components | wt % |
|---|---|
| Rosin | 7 |
| Tricresyl phosphate | 3 |
| Talc | 20 |
| Barium sulfate | 15 |
| Red iron oxide | 10 |
| Xylene | 20 |
| Methyl isobutyl ketone | 10 |
|  | 100 |
| Formulation example 4 | |
| Compound of formula (1) | 5 |
| CR-10 (chloride rubber resin of Asahi Denka Co.) | 13 |
| Zinc oxide | 20 |
| Talc | 20 |
| Plasticizer | 2 |
| Red iron oxide | 10 |
| Xylene | 30 |
|  | 100 |

When the agent for preventing adhesion of organisms of the present invention is used in the form of a solution, the adhesion and propagation of aquatic organisms can be avoided by, for example, dissolving the iodopropargylamine compound as an active ingredient and a film forming ingredient in a solvent to prepare a solution and applying it to a culturing net or fixed shore net.

A synthetic resin, artificial rubber, natural resin or the like are used as the film forming ingredient and xylene, toluene, cumene, methyl ethyl ketone, methyl isobutyl ketone, acetone and the like are used as the solvent.

An additive such as a plasticizer may be further used as required.

In the case of preparation of a solution, the iodopropargylamine compound as an active ingredient has no upper limit of concentration as far as a solution can be formed. However, it is generally used in an amount of 1 to 50 wt %, preferably 5 to 30 wt % based on the weight of the solution.

Examples of formulation in the case that the agent for preventing adhesion of organisms of the present invention is used as a solution are given below. However, it is not limited to these.

| Components | wt % |
|---|---|
| Formulation example 6 | |
| Compound of formula (1) | 15 |
| Acrylic resin (50% xylene solution) | 50 |
| Xylene | 35 |
|  | 100 |
| Formulation example 7 | |
| Compound of formula (1) | 10 |
| Acrylic resin (50% xylene solution) | 40 |
| Di-tert-nonyl pentasulfide | 5 |
| Liquid paraffin | 5 |
| Xylene | 40 |
|  | 100 |

When the agent for preventing adhesion of organisms of the present invention is used in the form of an emulsion, in accordance with a general method which has normally used to prepare an emulsion, a desired emulsion can be prepared by adding a surfactant to a solution of the iodopropargylamine compound as an active ingredient, and the surfactant which can be used is not limited to a particular kind.

The prepared medium can be used though kneading into a raw material such as a polymer resin for culturing nets and fixed shore nets used in the sea or underwater.

In the case of preparation of an emulsion, the iodopropargylamine compound as an active ingredient has no upper limit of concentration as far as an emulsion can be formed. However, it is generally used in an amount of 1 to 50 wt %, preferably 3 to 30 wt % based on the weight of the emulsion.

The above solution or emulsion of the present invention may be added to service water, reservoir water and the like to prevent the adhesion and propagation of aquatic organisms in the intake channels of cooling water or reservoirs.

BEST MODE FOR CARRYING OUT THE INVENTION

The compound and agents containing the same of the present invention will be specifically described in detail with reference to Synthesis Examples and Examples. However, it is not intend to limit the present invention into these.

A description is first given of Synthesis Examples.

SYNTHESIS EXAMPLE 1

Synthesis of diethyl 3-iodo-1,1-dimethylpropargylaminomethylene malonate (compound 3)

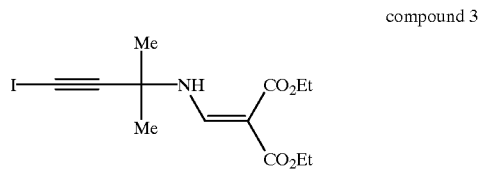

compound 3

4.15 g (50 mmol) of 1,1-dimethylpropargylamine and 10.8 g (50 mmol) of diethyl ethoxymethylene malonate were stirred in 150 ml of ethanol at 15° C. for 10 hours.

After ethanol was distilled off under reduced pressure, the residue was washed with a mixed solvent of diethyl ether and n-hexane (weight ratio of ⅓) to obtain 11.0 g of diethyl 1,1-dimethylpropargylaminomethylene malonate in the form of a white solid.

6.3 g (25 mmol) of the obtained diethyl 1,1-dimethylpropargylaminomethylene malonate was dissolved in 100 ml of methanol, and 6.3 g (25 mmol) of iodine and 2.5 g (28 mmol) of 45 wt % sodium hydroxide were each divided into 5 parts and added alternately at 0 to 10° C.

After 1.5 hour of stirring at 10° C., methanol was distilled off under reduced pressure and the residue was dissolved in chloroform.

The chloroform solution was washed with an aqueous solution of sodium thiosulfate and water in turn, dried over anhydrous magnesium sulfate, and then chloroform was distilled off under reduced pressure.

The obtained residue was washed with n-hexane to obtain 6.8 g of final compound.

The melting point of the compound was 100.0 to 101.0° C.

SYNTHESIS EXAMPLES 2 TO 14

Compound 1, compound 2 and compounds 4 to 14 were obtained in the same manner as in Synthesis Example 1.

The melting points and structural formulae of the compounds are given below.

compound 1 (melting point of 112.0 to 115.0° C.)
compound 2 (melting point of 178.0 to 179.0° C.)
compound 4 (melting point of 197.0 to 199.0° C.)
compound 5 (melting point of 128.0 to 130.0° C.)
compound 6 (melting point of 183.0 to 185.0° C.)
compound 7 (melting point of 99.0 to 101.0° C.)
compound 8 (melting point of 173.5 to 175.0° C.)
compound 9 (melting point of 111.0 to 112.0° C.)
compound 10 (melting point of 219.0 to 222.0° C.)
compound 11 (melting point of 152.0 to 155.0° C.)
compound 12 (melting point of 132.0 to 133.0° C.)
compound 13 (melting point of 172.0 to 173.0° C.)
compound 14 (melting point of 177.0 to 178.0° C.)

Next, the present invention will be described with reference to Examples showing the biological effect of each agent.

Example 1 (Evaluation of Antibacterial and Antifungal Activities)

6.6 ml of *Bacillus subtilis* to be tested was added to 125 ml of NB culture medium (Eiken Kagaku Co.) and 31.3 ml of *Trichophyton mentagrophytes* to be tested was added to 125 ml of a potato dextrose agar culture medium (Nissui Seiyaku Co.). The each medium was stirred not to foam the solutions, poured into plates uniformly and solidified.

Thereafter, a predetermined amount of each of compound 1, compound 2, compound 3, compound 5 and compound 9 was weighted and diluted with acetone to a predetermined concentration.

Paper disks were impregnated with respective samples containing predetermined amounts of the prepared compound 1, compound 2, compound 3, compound 5 and compound 9, laid on a filter, dried with air and placed on a plate containing each test microbe at equal intervals.

Bacillus subtilis was cultured at 37° C. for 1 day and Trichophyton mentagrophytes was cultured at 28° C. for 3 days in a thermostatic chamber and the diameter of each inhibiting zone was measured to evaluate the activity of each compound.

Results obtained with samples having a concentration of 100 ppm are shown in Table 2. Symbols in the table mean the followings;

A: *Bacillus subtilis*,

B: *Trichophyton mentagrophytes*,

+: inhibiting zone (A: 10 to 13 mm; B: 10 to 20 mm) is observed,

−: no inhibiting zone is observed.

TABLE 2

Antibacterial and antifungal activities

| Compounds | Judgment A | B |
|---|---|---|
| 1 | − | + |
| 2 | + | − |
| 3 | + | + |
| 5 | + | |
| 9 | + | |

Example 2 (Evaluation of Antibacterial and Antifungal Activities)

Series of diluted samples (20000, 10000, 5000, 2500, 1250, 626, 313, 156, 78 and 39 mg/l) of compound 3, compound 9, compound 10, compound 11, compound 12, compound 13 and compound 14 were prepared using dimethylsulfoxide.

A sensitive culture medium-N (Nissui Seiyaku Co.) was used for bacteria and a potato dextrose agar culture medium (Nissui Seiyaku Co.) was used for fungi. 0.5 ml of each sample was added to and mixed with 9.5 ml of the culture medium, poured into a Petri dish and solidified to obtain a plate.

As a result, the concentration of the compound in the agar culture medium was 1000, 500, 250, 125, 62.5, 31.3, 15.6, 7.8, 3.9 and 2.0 mg/l.

The bacteria to be inoculated were cultured in a bouillon for the assay of sensitivity (Nissui Seiyaku Co.) at 37° C. for 20 hours.

The fungi were cultured in the potato dextrose agar culture medium (Nissui Seiyaku Co.) for 10 days and then a $10^6$ CFU/ml suspension was prepared from each of them.

A test bacteria or fungi suspension was streaked on an agar plate containing the compound of the present invention and the agar plate was cultured at 37±1° C. for 18 to 20 hours for bacteria or at 27° C. for 7 days for fungi. A concentration at which no growth was seen was taken as minimum inhibitory concentration (MIC).

Results are shown in Table 3, Table 4 and Table 5. Symbols in the tables mean the followings;

A: *Bacillus subtilis*,

B: *Trichophyton mentagrophytes*,

C: *Rhodotorula mucilaginosa*,

D: *Staphylococcus aureus*,

E: *Aspergillus niger*,

F: *Penicillium funiculosum*,

G: *Candida albicans*.

TABLE 3

Antibacterial and antifungal activities

| Compounds | MIC (mg/l) A | B | C |
|---|---|---|---|
| 9 | 15.6 | 3.9 | 15.6 |
| 10 | 15.6 | 31.3 | |
| 11 | 15.6 | 15.6 | |
| 12 | 15.6 | 3.9 | |
| 13 | 15.6 | 3.9 | |
| 14 | 15.6 | 15.6 | |

TABLE 4

Antibacterial activity

| Compounds | MIC (mg/l) A | D |
|---|---|---|
| 3 | 31.3 | 31.3 |
| 9 | 15.6 | 15.6 |
| 12 | | 62.5 |

TABLE 5

Antifungal activity

| Compounds | MIC (mg/l) B | E | F | G |
|---|---|---|---|---|
| 3 | 15.6 | 3.9 | | 3.9 |
| 9 | 3.9 | 3.9 | 15.6 | 15.6 |
| 12 | 15.6 | | 31.3 | |

Example 3 (Evaluation of Anti-Legionella Activity)

A dimethyl sulfoxide solution of compound 9 having a concentration of 2000 mg/l was prepared. 1 ml of the solution was diluted with 19 ml of sterilized city water to prepare a solution having a concentration of 100 mg/l.

0.1 ml of a test bacteria solution (*Legionella pneumophila*) having a concentration of $3.1 \times 10^8$/ml was innoculated in 20 ml of the sample solution.

After the bacteria were contacted to the solution at 30° C. for 24 hours, the number of bacteria was counted.

Results are shown in Table 6.

TABLE 6

Anti-Legionella activity

| Compounds | Number of survival cells/ml after 24 hours |
|---|---|
| 9 | $<1.0 \times 10$ |
| Control | $1.2 \times 10^6$ |

Example 4 (Evaluation of Activity of Inhibiting Propagation of Freshwater Green Alga)

A predetermined amount of each of compound 2, compound 4, compound 9, compound 12, compound 13 and compound 14 was dissolved in culture media containing $10^5$/ml of freshwater green alga (*Selenastrum capricornutum*) at a logarithmic growth phase to prepare samples having a concentration of the compound in the medium of 500 ppb. The samples were left to stand and cultured at 23±1° C. for 24 hours under continuous illumination.

After 72 hours, a hemacytometer was employed to count the number of cells to obtain propagation rate.

The propagation inhibiting rate was calculated from comparison with the non-treated lot.

The results are shown in Table 7.

TABLE 7

Activity against freshwater green alga

| Compounds | Propagation Inhibiting rate (%) 500 ppb |
|---|---|
| 2 | 41 |
| 4 | 52 |
| 9 | 77 |
| 12 | 41 |
| 13 | 90 |
| 14 | 79 |

Example 5 (Evaluation of Activity of Inhibiting Propagation of Seawater Diatom)

A predetermined amount of each of compound 2, compound 3, compound 4, compound 5, compound 9 and compound 12 was dissolved in culture media containing $10^5$/ml of a seawater diatom (*Nitzschia closterium*) at a logarithmic growth phase to prepare samples having a concentration of the compound in the medium of 500 ppb. The samples were left to stand and cultured at 22±1° C. for 24 hours under continuous illumination.

After 72 hours, cells were collected by centrifugation and disrupted by addition of methanol to extract chlorophyll, and the amount of chlorophyll was measured from absorbance using a spectrophotometer to obtain propagation rate.

The propagation inhibiting rate was calculated from comparison with the non-treated lot.

The results are shown in Table 8.

TABLE 8

Activity against seawater diatom

| Compounds | Propagation inhibiting rate (%) 500 ppb |
|---|---|
| 2 | 51 |
| 3 | 46 |
| 4 | 45 |
| 5 | 46 |
| 9 | 93 |
| 12 | 69 |

Example 6 (Evaluation of Activity of Inhibiting Propagation of Freshwater Algae)

A predetermined amount of compound 9 was dissolved in a culture media containing $10^5$/ml of a freshwater alga at a logarithmic growth phase to prepare a sample having a concentration of compound 9 in the medium of 500 ppb. A shaking culture was performed at 100 rpm under continuous illumination for 24 hours at 20±2° C. for freshwater diatom and at 23±2° C. for other algae.

After 72 hours and 168 hours respectively, the total volume of cells was measured using a hemacytometer to obtain propagation rate.

The propagation inhibiting rate was calculated from comparison with the non-treated lot.

The results are shown in Table 9. Symbols in the table mean the followings;

A: freshwater green alga (*Chlorella pyrenoidosa*),

B: freshwater diatom (*Diatoma elongatum*),

C: freshwater green alga (*Scenedesmus pannonicus*),

D: freshwater green alga (*Ankistrodesmus falcutus*),

E: freshwater green alga (*Chlamydomonas reinhardii*).

TABLE 9

Activity against freshwater algae

| Algae | Propagation inhibiting rate (%) 500 ppb | |
|---|---|---|
| | 72 hr | 168 hr |
| A | 80 | 61 |
| B | 83 | 87 |
| C | 64 | |
| D | 84 | 62 |
| E | 74 | 52 |

Example 7 (Evaluation of Antifouling Activity Against Blue Mussel)

Compound 7 was completely dissolved in 1 ml of acetone and the resulting solution was uniformly applied to a 4 cm-diameter zone drawn on a test plate.

A zone coated with acetone only as blank and zones coated with 1.0 mg and 0.5 mg of copper sulfate as a comparison chemical were also prepared.

After drying, four blue mussel having a shell length of about 2 to 2.5 cm were adhered around each zone using a rubber piece as a spacer.

The thus prepared test plate was immersed in a water tank to which seawater ran and left to stand in the dark for 3 hours.

The adhesion controlling effect (adhesion repellent activity) was obtained from comparison with copper sulfate used as a comparison chemical.

The evaluation of adhesion repellent activity was based on "Evaluation method of adhesion repellent substance to marine adhesion organisms using *Mytilus edulis*" written by Kazuo Ina and Hideo Etoh (Chemistry and Biology, vol. 28 (No. 2), pp. 132–138, 1990).

The results are shown in Table 10, Symbols in the table mean the followings;

++: not adhered in the zone and strong repellent effect is observed,

+: adhesion in zone is observed but most of them adhered out of zone and repellent effect is observed, −: adhered in and out of zone alike and repellent effect is not observed.

TABLE 10

| Adhesion repellent activity against blue mussel | | |
|---|---|---|
| Compounds | Amount of chemical (mg) | Judgment |
| Compound 7 | 2.2 | ++ |
|  | 1.1 | + |
| Copper sulfate | 1.0 | + |
|  | 0.5 |  |
| Blank |  |  |

Industrial Applicability

The iodopropargylamine compound of the general formula (1) has high safety and exhibits a wide spectrum with a small amount, so that it is useful as an industrial antibacterial and antifungal agent, algicide or agent for preventing adhesion of organisms.

What is claimed is:

1. An iodopropargylamine amine compound of the following general formula (1):

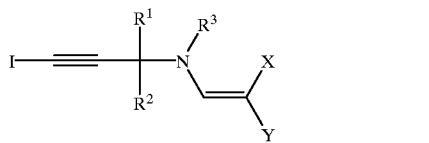

wherein $R^1$ and $R^2$ each independently represent a hydrogen atom or an alkyl group having 1 to 3 carbon atoms, or $R^1$ and $R^2$ combine with each other to form a tetramethylene group or a pentamethylene group, $R^3$ represents a hydrogen atom or an alkyl group having 1 to 3 carbon atoms, and X and Y each independently represent a cyano group, an alkoxycarbonyl group having 2 to 7 carbon atoms, an alkylcarbonyl group having 2 to 7 carbon atoms, an alkylsulfonyl group having 1 to 6 carbon atoms, a phenylcarbonyl group or a phenylsulfonyl group, provided that the phenyl group of a phenylcarbonyl group or a phenylsulfonyl group may be optionally substituted by halogen atoms, alkyl groups having 1 to 3 carbon atoms, alkoxy groups having 1 to 3 carbon atoms, nitro groups or trifluoromethyl groups.

2. The iodopropargylamine compound according to claim 1 wherein $R^1$ and $R^2$ each independently represent a hydrogen atom or an alkyl group having 1 to 3 carbon atoms, or $R^1$ and $R^2$ combine with each other to form a tetramethylene group, and $R^3$ represents a hydrogen atom or an alkyl group having 1 to 3 carbon atoms, and X and Y each independently represent a cyano group, an alkoxycarbonyl group having 2 to 4 carbon atoms, an unsubstituted phenylcarbonyl group or an unsubstituted phenylsulfonyl group.

3. An industrial antibacterial and antifungal agent characterized by containing the iodopropargylamine compound according to claim 1.

4. An algicide characterized by containing the iodopropargylamine compound according to claim 1.

5. An agent for preventing adhesion of organisms characterized by containing the iodopropargylamine compound according to claim 1.

6. An industrial antibacterial and antifungal agent characterized by containing the iodopropargylamine compound according to claim 2.

7. An algicide characterized by containing the iodopropargylamine compound according to claim 2.

8. An agent for preventing adhesion of organisms characterized by containing the iodopropargyl amine compound according to claim 2.

* * * * *